(12) United States Patent
Schecter

(10) Patent No.: US 7,720,529 B1
(45) Date of Patent: May 18, 2010

(54) IMPLANTABLE THERAPEUTIC DEVICE CONTROL SYSTEM

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 433 days.

(21) Appl. No.: 11/768,343

(22) Filed: Jun. 26, 2007

(51) Int. Cl.
*A61B 5/04* (2006.01)
(52) U.S. Cl. ....................................... 600/513
(58) Field of Classification Search ................... 600/513
See application file for complete search history.

(56) References Cited

U.S. PATENT DOCUMENTS

| | | | | |
|---|---|---|---|---|
| 6,832,113 B2 * | 12/2004 | Belalcazar | ............... | 607/23 |
| 2005/0043895 A1 * | 2/2005 | Schechter | ............... | 702/19 |

* cited by examiner

*Primary Examiner*—Carl H Layno
*Assistant Examiner*—Yun Haeng Lee

(57) ABSTRACT

A control system for an implantable cardiac therapy device, the device defining a plurality of sensing vectors including at least one impedance sensing vector and operating under a set of a plurality of variable operating parameters that define conditions for delivery of therapy and wherein the control system evaluates signal quality from the at least one impedance sensing vector and, if the quality is sufficient to discern valvular events, the control system adjusts the set of operating parameters to dynamically improve cardiac performance, including synchrony with valvular events, and if the quality is insufficient to discern valvular events, but sufficient to discern peaks, the control system adjusts the set of operating parameters to dynamically improve cardiac performance independent of valvular events, and if the quality is insufficient to discern peaks, the control system adjusts the set of operating parameters to induce cardiac performance towards a defined performance goal.

9 Claims, 8 Drawing Sheets

IMPLANTABLE THERAPEUTIC DEVICE CONTROL SYSTEM

BACKGROUND OF THE INVENTION

1. Field of the Invention

The invention relates to the field of implantable cardiac stimulation devices and to improved systems and methods of adjusting implantable devices for individual patients.

2. Description of the Related Art

Numerous patients suffer from disease conditions that affect their cardiac performance. For example, diseased myocardium reduces the mechanical pumping capabilities of the heart. Damaged valves can limit the sealing capabilities of the heart reducing capacity for complete filling and/or emptying. Impaired conduction and/or abnormalities in intrinsic activation can result in inappropriate/impaired stimulation of the cardiac tissue.

Implantable cardiac stimulation devices have been developed to provide therapy for certain patients suffering impaired cardiac function. Implantable cardiac stimulation devices generally include an implantable stimulation pulse generator and a microprocessor based controller regulating operation of the device. Implantable cardiac stimulation devices also typically include one or more implantable leads which are configured for implantation to extend adjacent the patient's heart. The implantable leads typically include one or more electrodes. The electrodes can be configured for dedicated sensing or delivery of stimulation or can be configured for combined sensing and stimulation delivery functions. The implantable devices are generally adapted to automatically sense the patient's physiologic status and automatically generate and deliver stimulation for cardiac abnormalities.

As one example, implantable cardiac stimulation devices have been designed to improve congestive heart failure (CHF) symptoms in certain cardiomyopathy patients with electromechanical dysynchrony. As such devices are adapted to provide therapy to attempt to resynchronize the patient's cardiac activity, for example, ventricle-ventricle synchrony, such devices are frequently referred to as cardiac resynchronization therapy (CRT) devices. Existing CRT devices do not necessarily have algorithms or capacity for adjusting or optimizing interval timing between pacing stimuli in different locations. Many physicians implant CRT devices without modification of default programmed interval timing. Thus, existing CRT devices generally pace the right ventricle (RV) and the left ventricle (LV) simultaneously or at a fixed delay therebetween.

While such CRT devices have been shown to benefit a number of CHF patients, there remain a significant proportion of patients who exhibit substantially less beneficial response to existing cardiac resynchronization therapies. Thus, it will be understood that there exists a need for improved therapies, for example, improved designs of implantable stimulation devices and improved methods of operating existing implantable cardiac therapy device designs to extend beneficial therapies to a broader range of patients.

SUMMARY

At least certain aspects of the invention are based on emerging data that indicates that relatively small changes in interval timing of an implantable therapy device can significantly reduce dysynchrony and improve cardiac output in at least certain patients. Certain aspects of the invention are also responsive to phenomena in at least certain patients of change of their condition over time throughout an implantation period. An individual's cardiac activity can change acutely, for example, through progression of a CHF condition, and/or myocardial ischemia/infarction. A patient's cardiac activity can also change chronically, for example, via remodeling following cardiac resynchronization therapy. This can result in indications for change in an existing programmed set of interval timing operational parameters of an implantable device.

While systems exist for telemetrically communicating with an implanted device in the implanted state, for example, via a physician's programmer, to enable a clinician to adjust a programmed set of operational parameters, existing systems are relatively inconvenient and not necessarily responsive to indications for change in the programmed parameters in a timely manner. For example, existing systems generally require the presence of the implantee in a clinical environment such that an attending clinician can interrogate the implanted device, evaluate the patient's condition, and make any indicated adjustments. This places a time burden on both the implantee and attending clinician. Further, the implantee foregoes the potential benefits of a revision in their device's programming until their next follow-up clinical visit. Thus, certain aspects of the invention are also adapted to more timely and more accurately evaluating the needs of an implantee and making any indicated revisions or adjustments in the programming with reduced time and inconvenience burdens on the implantee and attending clinical personnel.

Additional aspects of the invention are directed to event timing relating to opening and closing of the heart valves. In certain implementations, a more relevant event is the closure of the aortic valve. Myocardial thickening that occurs after aortic valve closure is relatively work inefficient and can lead to detrimental remodeling secondary to regional strain mismatch of substantially normal contractile tissue neighboring dysynchronous myocardial segments. Event timing can also be evaluated relating to mitral valve opening and closing and aortic valve opening. Use of high resolution impedance measurements can provide data indicative of these events and can be further utilized to define isovolumic relaxation (IR), systolic ejection period (SEP), and isovolumic contraction (IC). These aspects allow the device to temporally relate signals monitored to systolic and diastolic time periods throughout the cardiac cycle.

Additional aspects are directed to event timing relating to times of myocardial contractility and relaxation or mechanical systole and diastole. In at least certain implementations, mechanical systole and diastole does not occur in all myocardium simultaneously. Delays in electrical activation corresponding to conduction abnormalities and/or myocardial processes such as infarction corresponding to mechanical abnormalities can cause dysynchronous mechanical events. Certain aspects of the invention are directed to reducing such dysynchrony by pre-excitation or stimulation of dysynchronous myocardial tissue. In certain embodiments, determination of such pre-excitation intervals or electromechanical correction factors is derived through analysis of intrinsic electrograms and impedance measurements.

In certain embodiments, an interface with external sensing devices is utilized to correlate with internally made measurements, for example, for verification of identification of valvular events and dysynchronous contractility patterns. For example, in one implementation, echocardiographic equipment can be used to perform ultrasonic imaging of the patient's tissue for echocardiographic identification of valvular events and contractility patterns. In certain implementations, extrathoracic impedance measurements can also be made to correlate and compare with internally made measurements, for example, via the implantable therapy device. These aspects can be utilized to confirm that intracardiac impedance measurements correlate with their identification of valvular events and myocardial systole and diastole, for example at time of implant and at subsequent follow-up clinical visits.

One embodiment includes a control system for an implantable cardiac therapy device, the implantable therapy device defining a plurality of sensing vectors including at least one impedance sensing vector and the therapy device operating under a set of a plurality of variable operating parameters that define conditions for delivery of therapy by the device and wherein the control system evaluates a signal quality from the at least one impedance sensing vector and, if the quality of the signals is sufficient to discern valvular events, the control system adjusts the set of operating parameters to dynamically improve cardiac performance, including synchrony with valvular events, and if the quality is insufficient to discern valvular events, but sufficient to discern peaks, the control system adjusts the set of operating parameters to dynamically improve cardiac performance independent of valvular events, and if the quality is insufficient to discern peaks, the control system adjusts the set of operating parameters to induce cardiac performance towards a defined performance goal.

Another embodiment includes a method of adjusting the operation of an implantable cardiac therapy device, the method comprising programming a set of a plurality of operational parameters such that the device can deliver therapy to a patient according to the programmed set of operational parameters, intrathoracically sensing impedance across one or more vectors arranged to traverse myocardial tissue, determining at least one indicator of physiologic performance, evaluating a quality of the sensed impedance with respect to a threshold, and if the impedance sensing quality exceeds the threshold, adjusting the programmed set of operational parameters to induce the at least one physiologic performance indicator towards a dynamic goal, else adjusting the programmed set of operational parameters to induce the at least one physiologic performance indicator towards a static goal.

A further embodiment includes an implantable cardiac therapy device that defines a plurality of sensing vectors including at least one impedance sensing vector and wherein the device operates under a set of a plurality of variable operating parameters that define conditions for delivery of therapy by the device and wherein the device evaluates impedance signals from the at least one impedance sensing vector and determines at least one index of the impedance signals during at least one of systolic phases and lusitropic phases of the cardiac cycles and wherein the device self-adjusts the set of operating parameters to achieve at least one of an increase in a systolic index and a decrease in a lusitropic index. These and other objects and advantages of the invention will become more apparent from the following description taken in conjunction with the accompanying drawings.

DETAILED DESCRIPTION

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
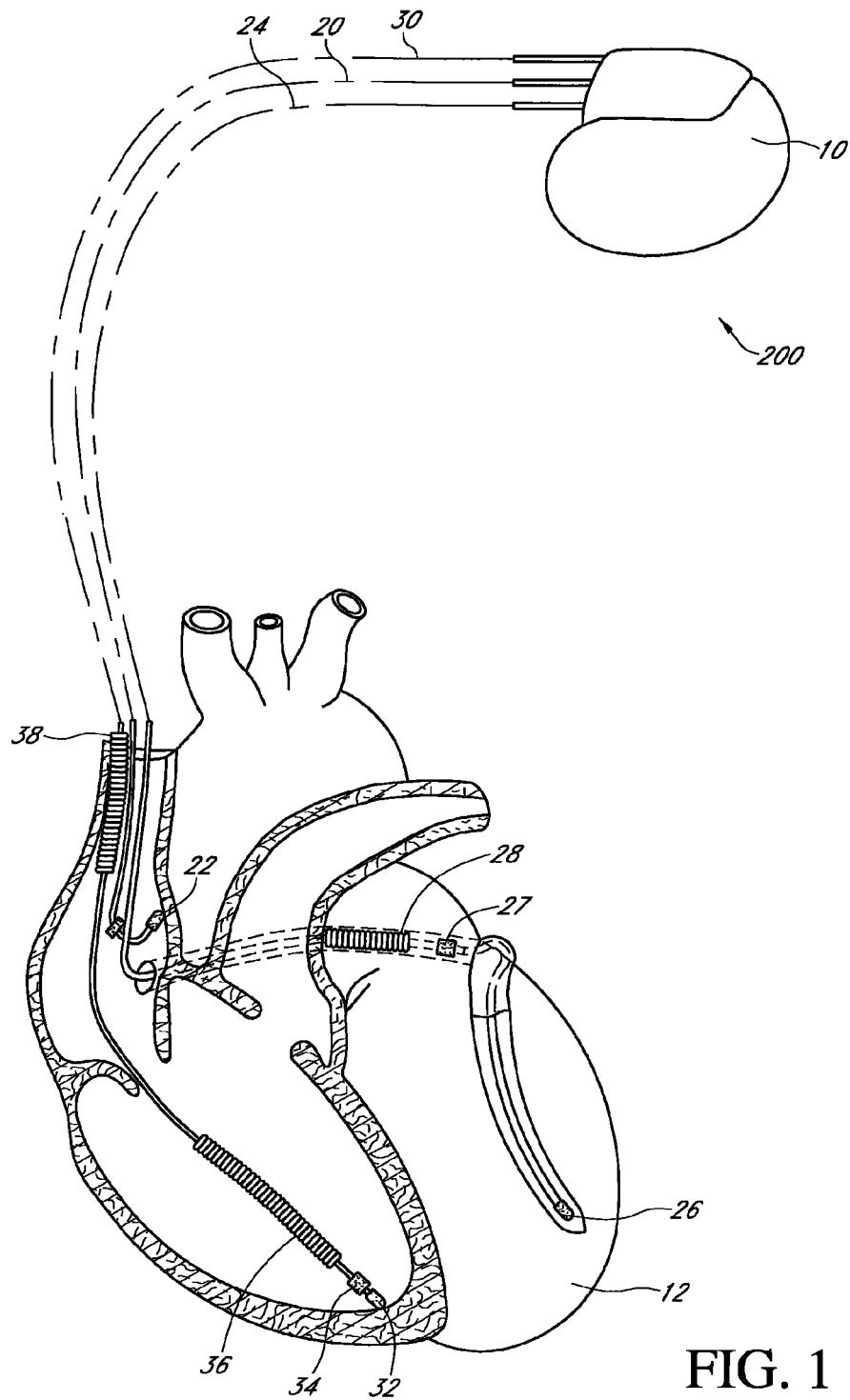
FIG. 1 is a simplified diagram illustrating a therapeutic appliance with an implantable stimulation device in electrical communication with at least three leads implanted into a patient's heart for delivering multi-chamber stimulation and shock therapy.

In one embodiment of a therapy system 200, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
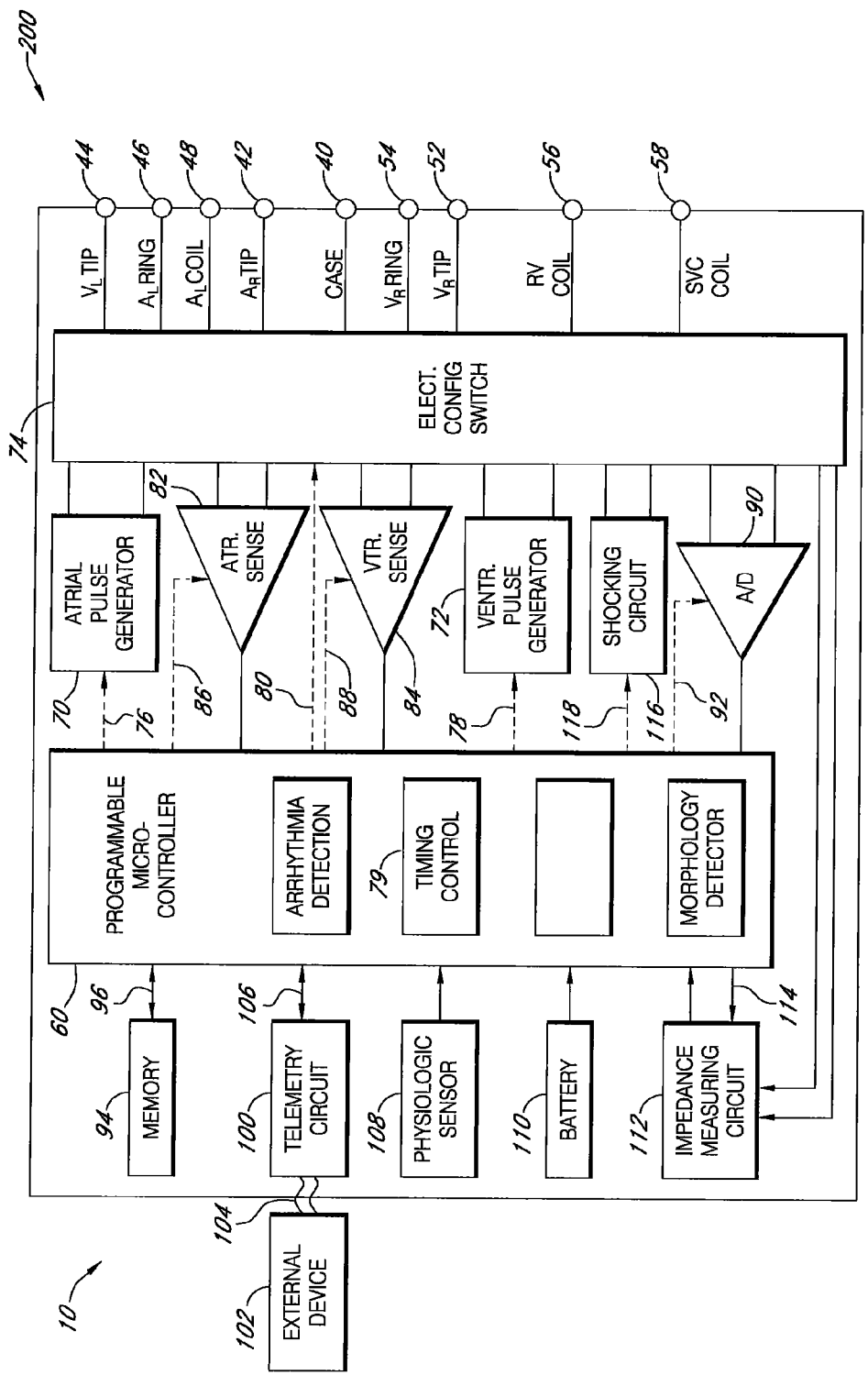
FIG. 2 is a functional block diagram of a multi-chamber implantable stimulation device illustrating elements of a stimulation device that can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all pacemaker "unipolar" modes. The housing 40 may further be used as a return electrode alone or in combination with one or more of the coil electrodes, 28, 36 and 38, for shocking purposes. The housing 40 further includes a connector having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high-resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart.

Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones)

and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (NO) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, timing/delays and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In certain preferred embodiments, the stimulation device 10 further includes a physiologic sensor 108, commonly referred to as a "rate-responsive" sensor because it can be used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 that provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monofluoride or a hybrid of the two.

As further shown in FIG. 2, the device 10 is shown as having an impedance measuring circuit 112 that is enabled by the microcontroller 60 via a control signal 114. The impedance measuring circuit 112 is adapted to provide a known current or voltage, measure a resulting voltage or current, and thereby determine an impedance of the interposed materials. In one embodiment, the circuit 112 is adapted to deliver pulses of approximately 200 µA and 30 µS width at a frequency of 128 Hz. Such pulses generally will not depolarize myocardium, cause limited battery drain, and operate at a frequency that acts as a band pass filter to improve signal to noise ratio of the sensed impedance. In certain embodiments, the impedance measuring circuit 112 preferably supports determinations of multiple impedance measurements, for example along multiple spatially arranged sensing vectors.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (Le., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
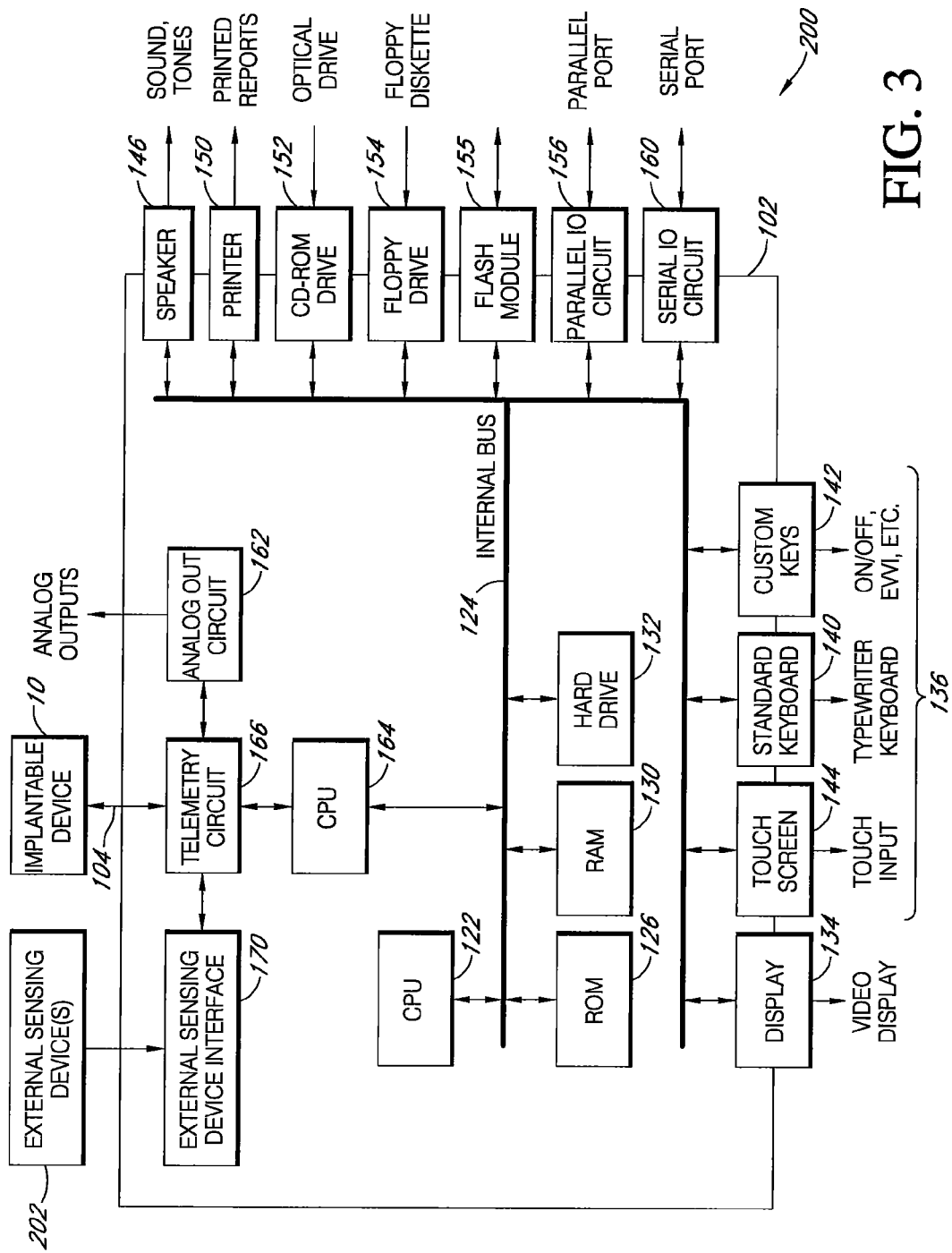
FIG. 3 is a functional block diagram of one embodiment of a physician's programmer capable of establishing communication with an implantable medical device and with one or more external sensing devices.

FIG. 3 is a functional block diagram of one embodiment of an external device 102, such as a physician's programmer. The external device 102 is adapted to provide connectivity with the implantable device 10 and with one or more external sensing devices 202. The external device 102 is further adapted to display data indicative of signals received from the implantable device 10 and the external sensing device(s) 202. The external device 102 is also adapted to send commands to the implantable device 10, for example to adjust the programming of the device 10.

In one embodiment, the external device 102 comprises a CPU 122 in communication with an internal bus 124. The internal bus 124 provides a common communication link and power supply between various electrical components of the external device 102, for example including the CPU 122. The external device 102 also comprises memory and data storage that can include one or more of ROM 126, RAM 130, and a hard drive 132 in communication with the internal bus 124. The ROM 126, RAM 130, and hard drive 132 provide temporary memory and non-volatile storage of data in a well-known manner. In one embodiment, the ROM 126, RAM 130, and/or hard drive 132 can store control programs and commands for upload to the implantable device 10 as well as operating software for display of data received from the implantable device 10 and/or from one or more external sensing devices 202. It will be appreciated that in certain embodiments alternative data storage/memory devices, such as flash memory, can be included or replace one or more of the ROM 126, RAM 130, and hard drive 132 without detracting from the spirit of the invention.

The external device 102 also comprises a display 134. The display 134 is adapted to visually present graphical and alphanumeric data in a manner well understood in the art. For example, in certain embodiments, the display 134 and the external device 102 are adapted to display waveforms indicative of a patient's physiologic activity based at least partially on signals received from the implantable device 10 and/or the one or more external sensing devices 202. In various implementations, the external device 102 is adapted to display one-dimensional curvilinear waveforms and/or two-dimensional images indicative of the patient's physiologic activity. The display 134 is also adapted to display status information for the implantable device 10, such as current programming settings.

The external device 102 also comprises one or more input devices 136 to enable a user to provide commands and input data to the external device 102. In one embodiment, the input devices 136 include a keyboard 140, a plurality of custom keys 142, and a touch screen 144 aspect of the display 134. The keyboard 140 facilitates entry of alphanumeric data into the external device 102. The custom keys 142 can be programmable to provide one touch functionality of predefined functions and/or operations. The custom keys 142 may be embodied as dedicated touch keys, such as associated with the keyboard 140 and/or predefined areas of the touch screen 144. In this embodiment, the external device 102 also comprises a speaker 146 and a printer 150 in communication with the internal bus 124. The speaker 146 is adapted to provide audible signals to a user. The printer 150 is adapted to provide a printed readout of information from the external device 102.

In one embodiment, the external device also comprises one or more of an optical drive 152, a floppy drive 154 and flash module 155 which together provide removable data storage. In this embodiment, the external device also includes one or more of a parallel input-output (IO) circuit 156, a serial IO circuit 160, and an analog output circuit 162. These circuits 156, 160, 162 provide a variety of communication capabilities between the external device 102 and other devices in a manner well understood in the art.

The external device 102 also comprises an external sensing device interface 170 adapted for communication with the one or more external sensing devices 202. In certain embodiments, the external sensing device interface 170 is adapted for wired communication with the one or more external sensing devices 202. In certain embodiments, the external sensing device interface 170 is adapted for wireless communication with the one or more external sensing devices 202. The external sensing device interface 170 can include amplifiers, A/D-D/A converters, bandpass filters, and/or overcurrent-overvoltage protection circuits depending on the requirements of specific applications.

The external sensing devices 202 provide data indicative of a patient's condition obtained from at least partially externally arranged sensing. It will be understood that in certain implementations, the external sensing devices 202 are adapted to sense patient physiologic activity that at least partially occurs within the patient's body. As used herein, external sensing refers to sensing, for example with one or more embodiments of the external sensing devices 202, wherein at least certain physical sensing components are arranged externally of the patient, for example on a skin surface. In certain embodiments, the external sensing devices 202 can employ radiated or transmitted energy, such as sonic energy and/or electromagnetic energy that propagates internally within the patient.

In one embodiment, the external sensing device 202 comprises a surface ECG sensor 202. The surface ECG sensor 202 includes a plurality of ECG leads that are adapted for placement on the patient's skin. The ECG sensor 202 obtains electrical signals from the surface of a patient's body and configures the signals for display as an ECG waveform on the display 134 of the external device 102.

In another embodiment, the external sensing devices 202 comprise an external impedance sensor 202. In this embodiment, the external impedance sensor 202 obtains electrical impedance measurements indicative of the time varying impedance of patient tissue and fluids/solids interposed between sensing electrodes. In certain embodiments, sensing electrodes of the external impedance sensor 202 are preferably arranged to define multiple spatial vectors such that impedance measurements can be obtained along multiple spatially arranged paths.

In a further embodiment, the external sensing devices 202 comprise an ultrasonic imager 202. The ultrasonic imager 202 is adapted to deliver sonic energy to the patient's body and sense at least one of reflected and transmitted sonic energy. The ultrasonic imager 202 can thus develop signals indicative of the internal structure and activity of the patient. In certain embodiments, the ultrasonic imager 202 is further adapted to perform continuous wave and/or pulsed Doppler measurements such that the ultrasonic imager 202 can also develop signals indicative of velocity characteristics of selected patient tissue/fluids. Impedance measurements and ultrasonic imaging can provide data indicative of mechanical properties of the patient as will be described in greater detail below. Additional details of systems and methods of external sensing devices 202 and operation thereof with an implantable stimulation device 10 that can be advantageously employed with the embodiments described and illustrated herein can be found in the co-owned application A05E4022 to Dr. Stuart Schecter entitled "MEDICAL EVALUATION AND THERAPY SYSTEM" which is incorporated herein in its entirety by reference.

The external device 102 also comprises telemetry CPU 163 and a telemetry circuit 166 that can establish the telemetric link 104 in cooperation with the implantable device 10 and optionally with one or more of the external sensing device(s) 202. The telemetric link 104 comprises a bidirectional link to enable the external device 102 and the implantable device 10, for example, to exchange data and/or commands. The establishment of the telemetric link 104 is, in certain embodiments, facilitated by a wand or programmer head that is placed in proximity to the implantable device 10. The wand or programmer head facilitates establishment of the telemetric link 104 by placing an antenna structure in a closer proximity to the implantable device 10 to facilitate conduction of transmitted signals to the external device 102.

The telemetric link 104 can comprise a variety of communication protocols appropriate to the needs and limitations of a given application. In certain embodiments, the telemetric link 104 comprises radio frequency (RF) telemetry. In one particular embodiment, the telemetric link 104 comprises a frequency modulated digital communication scheme wherein logic ones are transmitted at a first frequency A and logic zeros are transmitted at a second frequency B. As previously noted, the implantable device 10 is powered by a battery having limited capacity. In certain embodiments, the external device 102 is powered by line voltage, e.g., is not subject to the stringent power limitations of the implantable device 10.

Thus, in certain embodiments, the bidirectional telemetric link 104 can proceed in an asymmetric manner.

For example, in one embodiment, a transmission power and data rate from the external device 102 to the implantable device 10 via the telemetric link 104 can proceed at higher power levels and/or higher data transmission rates than the reciprocal data rates and transmission power from the implantable device 10 to the external device 102. The telemetry circuit 100 of the implantable device 10 as well as the telemetry circuit 166 and CPU 164 of the external device 102 can select or be adjusted to provide a desired communication protocol and transmission power in a manner which will be well understood by one of ordinary skill.

The therapy system 200 is configured to measure and evaluate a patient's physiology and further adapted to adjust therapy delivery in an individualized manner to optimize the therapy for the needs and condition of the individual patient. As used herein, the terms "optimal", "optimize," "optimizing," "optimization", "minimize", "maximize" and the like are to be understood as commonly used terms of the art referring simply to a process of evaluating and adjusting or individualizing the operating parameters of a system for improved performance in an individual application. It will be understood that the physiologic activity and characteristics of an individual, for example their cardiac activity, is subject to both random variations, cyclical variations, diurnal variations, and long-term variations. An individual patient's physiologic activity is also subject to variation brought about by medication dosing. Environmental factors and noise are generally asynchronous and unpredictable by an automated therapy system and can, at least in certain implementations, impair complete isolation of signals of interest.

Thus, the matching of therapy systems and methods to precise instantaneous needs of a patient is, as a practical matter, an inexact science. Thus, use of the terms "optimal", "optimize," "optimizing," "optimization" and the like does not imply that the described process results in a perfect setting for a system or method as used with an individual patient or that any further improvements are not available. Thus, the terms "optimize," "optimizing," and/or "optimization" are to be interpreted as relative terms indicating generally improved performance in an individual application and are not to be interpreted as absolutes.

Figure 4:
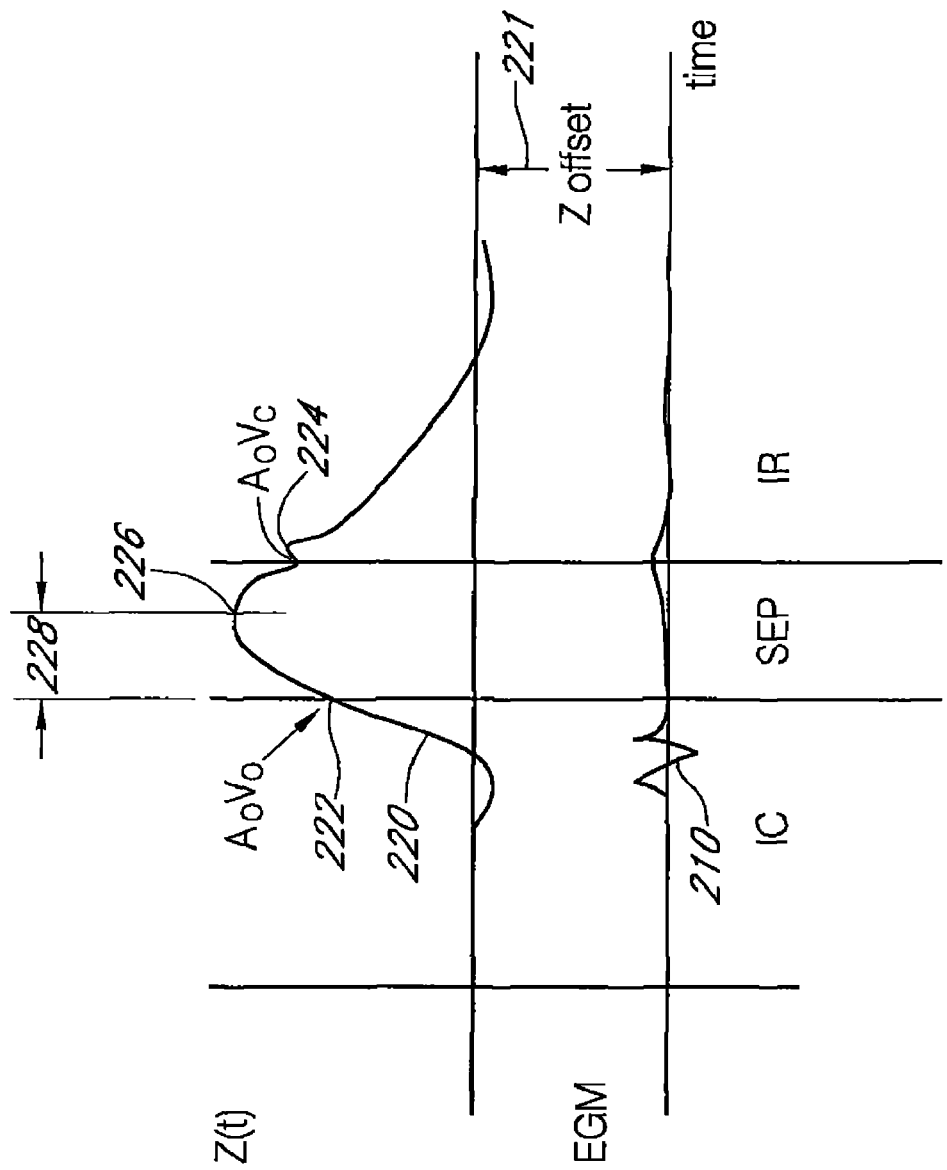
FIG. 4 illustrates exemplary waveforms indicative of physiologic activity, including an impedance curve and a cardiac electrogram.

FIG. 4 illustrates one embodiment of waveforms indicative of a patient's physiologic activity. In this embodiment, includes an electrogram waveform 210 corresponding to time varying electric signals indicative of the patient's cardiac activity and an impedance waveform 220 corresponding to time varying impedance indicative of myocardial thickening and thinning, ejection and filling of blood, and valvular events. As previously noted, in certain embodiments, it is preferred to obtain measurements indicative of the patient's physiological activity via implantable sensing devices, such as provided by the device 10. Thus, in certain embodiments, the waveforms 210 and 220 correspond to internally made measurements.

The waveform 220 exhibits a baseline offset 221. The offset 221 corresponds generally to cardio-thoracic resistivity/impedance. The offset 221 relates to relatively static physiologic structures within the thorax as well as dynamically changing components, such as thoracic fluid volume. Thus while the offset 221 would generally include time varying components, the time varying aspects of the offset 221 have different time and frequency domain characteristics than the time varying waveform 220 corresponding to the patient's cyclical cardiac activity. In certain embodiments, data corresponding to the observed offset 221 can be stored and analyzed over time, for example to develop trend information. These aspects facilitate monitoring for possible deterioration or improvement in the patient's condition and can be further utilized as a factor in setting alarms, for example to alert a physician for possible revision of the patient's therapy.

In this embodiment, the impedance waveform 220 exhibits a characteristic monument 222 corresponding to aortic valve opening and a second characteristic monument 224 corresponding to aortic valve closing. Interposed between the first and second monuments 222, 224, is a peak impedance 226. The peak impedance 226 corresponds generally to peak myocardial thickening and minimal blood volume.

A delay or interval 228 is also defined as the time from the aortic valve opening monument 222 and the peak impedance 226. The delay or interval 228 from aortic valve opening 222 to peak impedance 226 as well as the morphology of the aortic valve opening and closing monuments 222, 224 are indicative of specific pathological processes. These processes can include aortic stenosis, and/or regurgitation and may also be indicative of decreased cardiac output. As certain impedance sensing vectors may have difficulty discerning the aortic valve opening and/or closing monuments or notches, an electrode arrangement defining a vector substantially traversing the aortic valve will be preferred for obtaining such impedance signals.

As previously noted, in certain embodiments it is preferred that the capability be provided to sense impedance across a plurality of different sensing vectors to facilitate determination of regional properties. In one embodiment, right heart impedance sensing can be performed by applying current between a RA ring and RV tip electrodes with the RA tip and RV ring electrodes used for corresponding sensing. In another embodiment, current pulses can be delivered between the RV tip and can/housing electrodes and a corresponding voltage measurement made between the RV ring and RV coil electrodes to determine RV impedance curve data. Similarly, current can be delivered between the RV tip and can and corresponding voltage sensed between the RV ring and LV tip electrodes. In another embodiment, sensing vectors can be defined between the LV and RV apical electrodes and the SVC and LV electrodes. Delivering current between the RV tip and SVC/can electrodes with corresponding voltage measurements being made between the RV ring and RV coil and the RV ring and LV tip electrodes can provide more globally indicative data.

Impedance measurements can be obtained over multiple cardiac cycles and the results of each cycle can be post-processed, for example, by ensemble averaging techniques to generate representative impedance characteristics having improved signal to noise. Measurements taken across multiple vectors can also be combined to generate one or more "global" impedance signals. In various embodiments, measurements across multiple vectors can be performed substantially simultaneously and/or separated in time. In certain embodiments, the device 10 can perform post-processing by ensemble averaging of multiple impedance signals along one vector to improve the signal to noise ratio. In certain embodiments, the device can perform post-processing by summation averaging along more than one vector of an ensemble averaged impedance signal acquired along one vector to improve signal to noise ratio.

Figure 5:
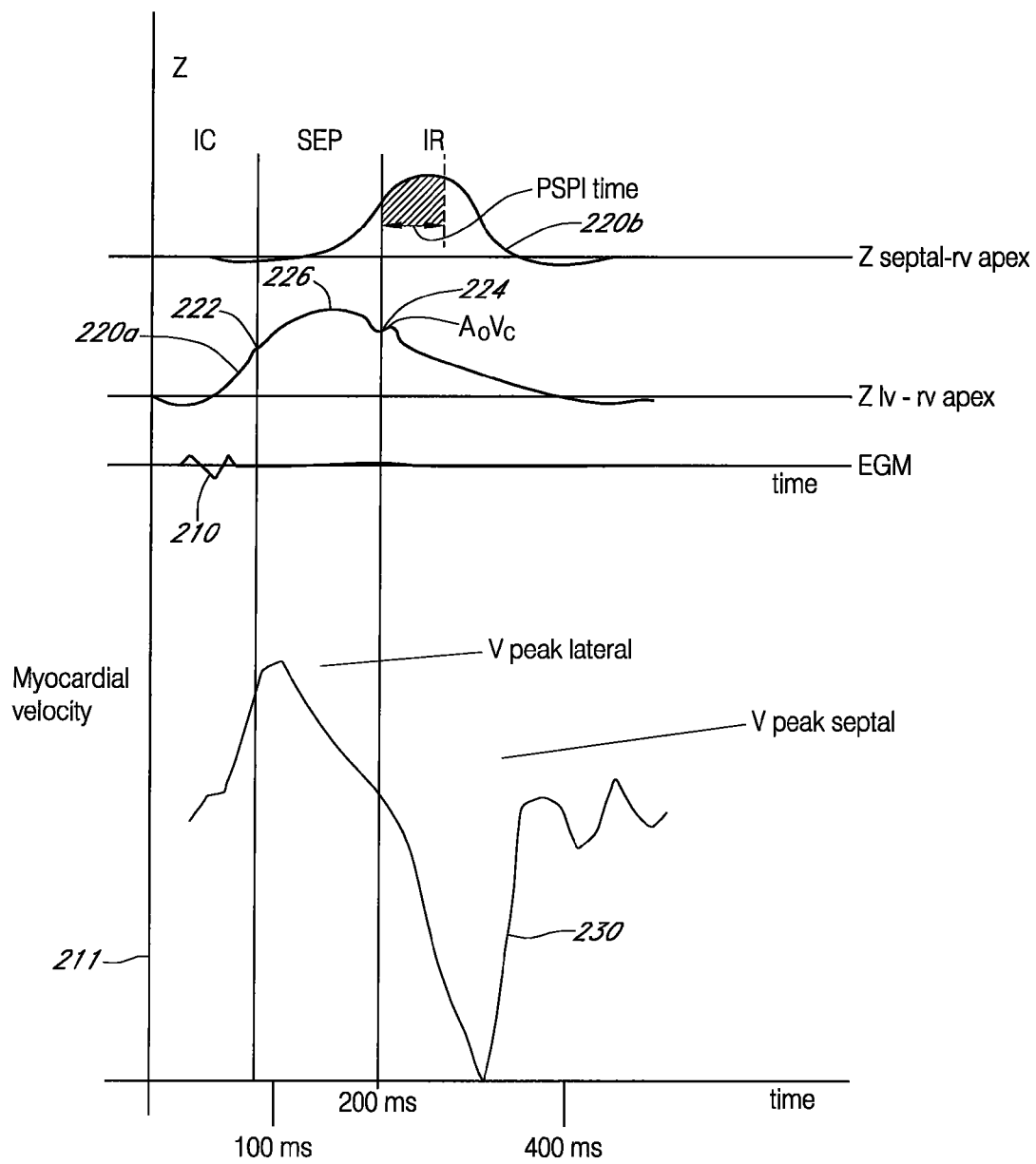
FIG. 5 illustrates additional exemplary waveforms indicative of physiologic activity, including impedance curves measured along different vectors, a velocity profile, and a cardiac electrogram.

FIG. 5 illustrates another embodiment of waveforms indicative of a patient's physiological activity, and in this embodiment, including impedance measurements from a plurality of sensing vectors. In this embodiment, a first impedance waveform 220a is illustrated, corresponding to impedance measurements made along a vector arranged between the left ventricle and right ventricle apex. This embodiment also includes a second impedance waveform 220b measured along a central to right ventricle apex vector. It will be understood that in other embodiments, additional impedance vectors can likewise be obtained and evaluated.

Multiple vector impedance measurements obtained between a plurality of sensing locations arranged about the patient's heart 12 can be combined to define global impedance data to further improve signal definition, for example to better define aortic valve events. Multiple integration techniques and/or use of summation averaging techniques can also be employed to improve the signal processing of such impedance data. Use of external sensing devices 202, such as ultrasonic imaging devices performing echocardiographic measurements can also be utilized in evaluating the patient's physiologic performance. For example, in this embodiment, a waveform 230 is illustrated corresponding to myocardial velocities.

In this embodiment, the patient's physiologic activity can be evaluated with respect to the onset 211 of the EGM signal 210. In this embodiment, aortic valve opening 222 occurs approximately 100 milliseconds after EGM onset 211. Aortic valve closure 224 occurs approximately 200 milliseconds after EGM onset 211. Septal contractility occurs generally after aortic valve closure 224 with peak septal contractility occurring at approximately 300 milliseconds after EGM onset 211.

As impedance values over time can be observed across specific myocardial segments between given electrodes, information about regional myocardial thickening/thinning can be derived. Such information can include time of peak myocardial thickening as well as relative degree of myocardial thickening. Such data can then be utilized to identify changes in timing as well as degree of local contractility. As the timing of contractility can be based on identification of peak impedance along a specific segment or vector, the demands for high resolution signal quality are reduced.

In embodiments where higher resolution impedance signals are available, additional data can be derived. Again, confirmation that a given impedance signal provides satisfactory identification of event timing (such as valvular activity) can be made via comparison with external measurements, such as echocardiographic data. This will facilitate repeat assessment of timing of valvular events with intrinsic or internally sensed impedance data to facilitate making changes in interval timing and reprogramming of a device 10. For example, in certain implementations, the timing of aortic valvular events may change, for example resulting in a shorter systolic ejection period, upon other interval timing changes. The ability to identify valvular events via impedance measurements greatly facilitates self-assessment of activity via the device 10.

Figure 6:
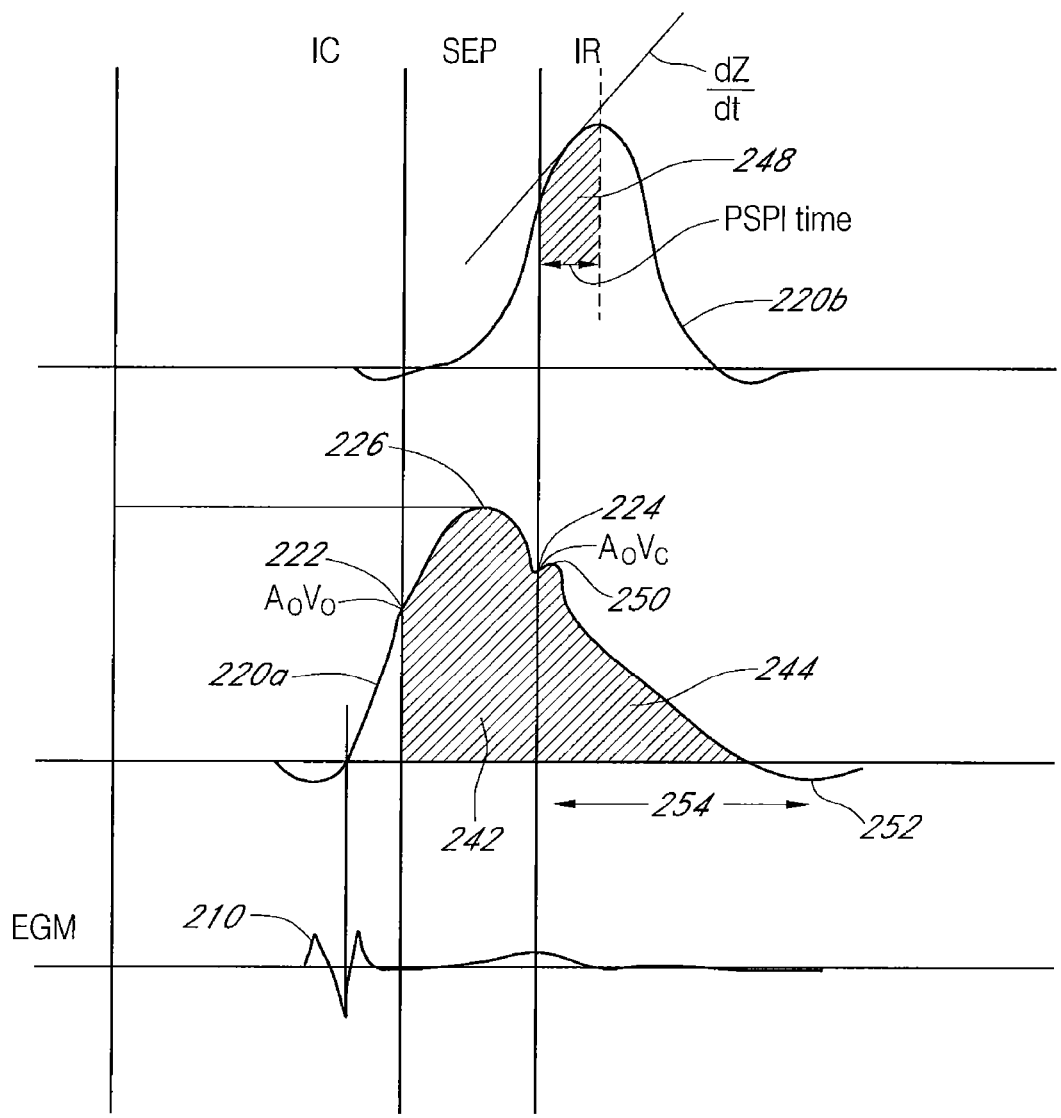
FIG. 6 illustrates further exemplary waveforms and characteristics of impedance signals that can be evaluated to adjust the programming of operational parameters of an implantable therapy device for improved physiologic performance.

FIG. 6 illustrates further embodiments of parameters or characteristics of a patient's physiologic activity that can be evaluated and utilized by an implantable device 10 to optimize the operation of the device 10 for improved patient performance. In this embodiment, impedance measurements can be utilized to determine a systolic cardiac performance (SCP) indicator. The SCP indicator 242 corresponds generally to an integral or area under the impedance curve 220a generally between the aortic valve opening event 222 and the aortic valve closing event 224. In another embodiment, the SCP index 242 can be determined as the integral of the impedance curve 220a from the IEGM onset 211 to the peak impedance event 226. The SCP index or indicator 242 corresponds generally to the patient's total systolic output. Generally, a higher SCP indicator 242 would correlate to improved or higher cardiac pumping output performance.

As illustrated in FIG. 6, in this embodiment a lusitropic cardiac performance (LCP) index 242 can also be determined. In a similar manner to the SCP index 242, the LCP index 244 corresponds generally to an integral or area under the impedance curve between the aortic valve closure event 224 and the end of the diastole. In another embodiment, the LCP index 244 corresponds generally to the integral or area under the impedance curve between the impedance peak 226 and the end of diastole/beginning of the next cycle of systole. The LOP index 242 is indicative of the relaxation characteristics of the heart 12 with lower values of the LCP index 242 being generally associated with more desirable performance.

The SCP index 242 and LCP index 244 can also be utilized to determine a systolic-lusitropic index (SLI) 246. The SLI 246 is calculated as the ratio of the SCP index 242 to the LCP index 244 or $$SLI\ 246 = \frac{SCP\ 242}{LCP\ 244}$$

A larger value of the SCP index 242 generally corresponds to improved patient contractile or pumping cardiac performance. A lower value of the LCP index 244 corresponds generally to an improved lusitropic or chamber refilling performance. A higher numerator (SCP 242) and lower denominator (LCP 244) results in a larger quotient value of the SLI 246 indicating improved or better overall patient cardiac performance. Thus, in certain embodiments, adjustments are made in the programming of the device 10 to result in higher values of the SLI 246.

In at least certain implementations, a patient may exhibit a post-systolic positive impedance (PSPI) 248 as illustrated in FIG. 6. As previously noted, further cardiac contraction activity after aortic valve closure is work inefficient and generally does not contribute to further cardiac output. Thus, it will be preferred that any PSPI 248 be reduced as much as possible. Thus, in certain embodiments, adjustments are also made in the programmed operating parameters of the device 10 to reduce any PSPI 248 to as low a value as practical.

In certain embodiments, the device 10 is further adapted to evaluate the impedance signals and identify the onset of negative impedance slope and time of peak impedance adjacent diastole indicated generally as 250 of waveform 220a. The device 10 is further adapted to identify a nadir of impedance 252 following $A_OV_C$ for a cardiac cycle. In certain embodiments, the device 10 delineates the lusitropic phase 254 of the cardiac cycle by the time between peak impedance and/or onset of negative impedance slope 250 to the time of nadir of impedance 252.

Figure 7:
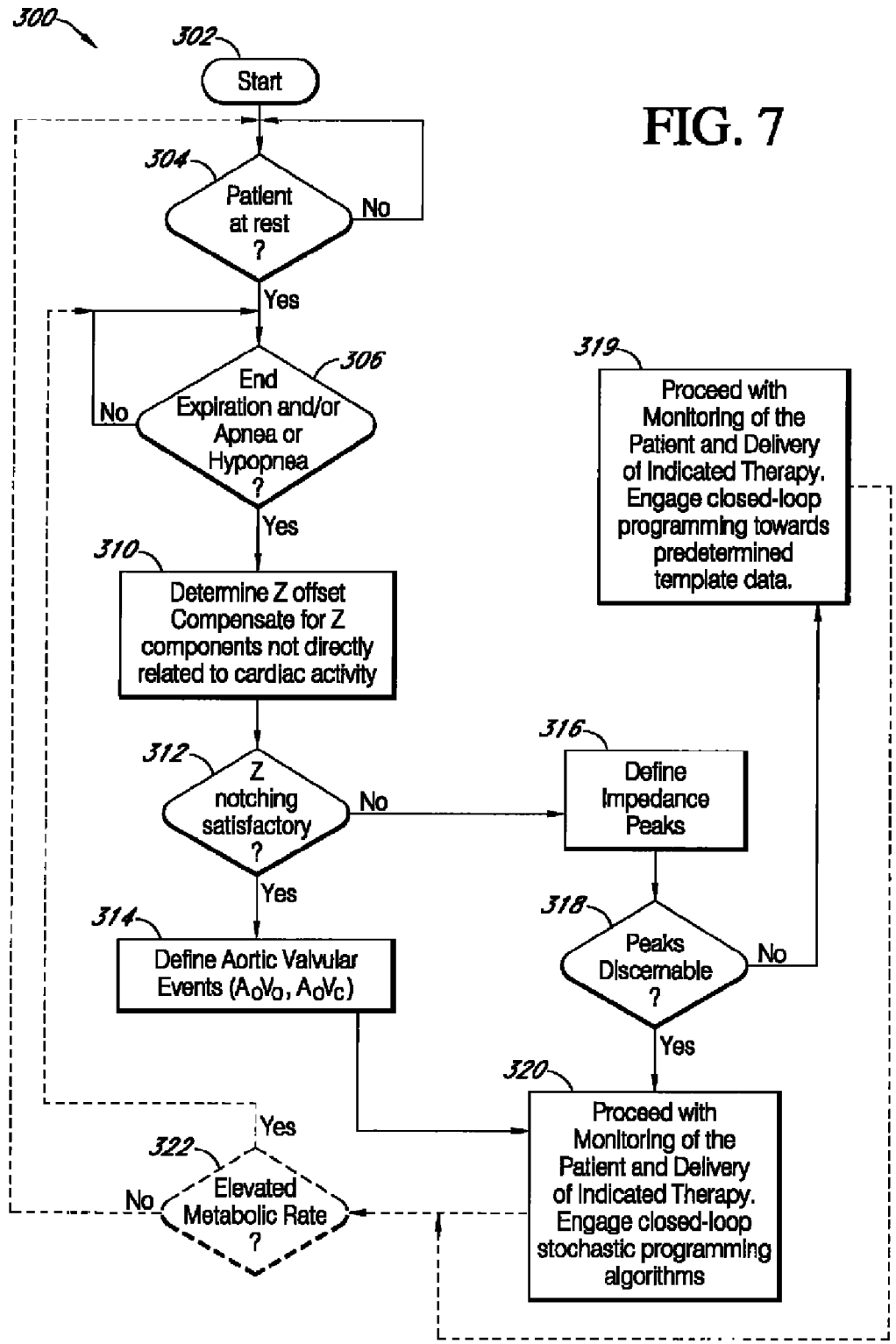
FIG. 7 is a flow chart of one embodiment of a system and method of defining impedance characteristics for refining the programming of an implantable therapy device.

FIG. 7 is a flowchart of one embodiment of a system and method 300 for evaluating and defining impedance characteristics for use in refining or optimizing the programming of an implantable therapy device 10. This embodiment begins in a start block 302 wherein a given device 10 would be implanted and initially programmed for the individual characteristics of the patient. In this embodiment, the start block 302 would proceed for some period of time to allow the implanted device and one or more patient leads to mature and become fibrosed into a stable position. This aspect allows the implanted device 10 and associated patient leads and the associated electrical characteristics of their interface with patient tissue to achieve a relatively stable level. The particular interval or duration for this maturation or fibrosis will vary for an individual patient, however, in many implementations will be approximately three months in length.

Once the maturation process has substantially elapsed, the method 300 proceeds to a block 304 wherein a determination is made whether the patient is at rest. As patient movement can introduce confounding signals complicating accurate analysis of impedance signals for determination of the patient's cardiac activity, in certain implementations it will be preferred that analysis of the impedance signals proceed while the patient is at rest. Thus, if the determination of block 304 is negative, the method 300 waits until such a rest period occurs.

When the determination of block 304 is affirmative, the system and method proceed to a block 306 wherein a determination is made whether the patient is at an end of an expiration phase of their respiration and/or if they are experiencing a period of apnea or hypopnea. Patient respiration and translation of the heart 12 can also introduce confounding signals complicating accurate analysis of the impedance characteristics for cardiac activity. Thus, the block 306 pauses further evaluation of the system and method 300 until it is determined that the patient is both at rest as determined by block 304 and that their respiration is relative quiescent as determined by block 306.

With both these conditions satisfied, the system and method 300 proceed with a block 310 wherein the impedance offset 221 (FIG. 4) is determined. The impedance offset 221 determination is directed to identifying impedance signal components not related directly to the patient's cardiac activity. For example, depending on the particular sensing vectors utilized, impedance changes related to the great vessels can have a relatively significant influence. For example, systolic forward blood flow can dramatically increase aortic blood volume that has a relatively low impedance value compared to thickening myocardium. Similarly, static structures within the thorax as well as dynamic changes in thoracic fluid volume can have relatively significant impedance components.

Block 310 is directed to identifying such impedance components not directly related to the patient's cardiac activity. Identification and compensation of this baseline or offset impedance 221 in block 310 facilitates identification of the time varying impedance components related to the patient's cardiac activity. It will be appreciated that as the baseline impedance includes components having a time-varying nature, for example, respiration components, the baseline or offset impedance signal is not a constant value over time. In certain embodiments, determination of the offset 221 in block 310 that is performed while patient rest and end of an expiration phase of their respiration and/or a period of apnea or hypopnea are both true, for example as from blocks 304 and 306 simplifies compensation for the offset 221. In certain embodiments, additional sensors such as accelerometers and/or minute ventilation sensors can provide data to be utilized in the block 310, for example, to identify and track patient respiration.

In certain embodiments, more accurate evaluation of impedance signals corresponding to cardiac activity can be made by avoiding using the device can or housing 40 as an electrode. At least certain sensing vectors utilizing the can or housing 40 as an electrode define vectors traversing a significant portion of lung parenchyma and the great vessels.

Normalizing the impedance signal or compensating for the baseline or offset 221 utilizing impedance data obtained between the superior vena cava (SVC) coil and can or housing 40 will help reduce signals related to the great vessels and respiratory variations in implementations utilizing the can or housing 40 as an electrode. In other embodiments, subtraction of an impedance component obtained from a vector arranged between the SVC and can from a composite intracardiac impedance signal will improve the signal to noise ratio and facilitate more accurate identification of the cardiac activity and suppression of confounding signals.

As previously mentioned, in certain implementations, it is preferred that the device 10 operate to optimize electromechanical synchrony. In certain implementations it is also generally preferred that the electromechanical contractile activity be maintained in synchrony with valvular activity. These implementations can be employed for example to reduce PSPI. Thus, in one embodiment, the system and method 300 includes an evaluation block 312 wherein a determination is made whether the signal resolution of the impedance is sufficient not only to identify contractile activity but also to identify valvular events, such as the events 222 and 224 relating to aortic valve opening and closure.

In certain implementations the evaluation of block 312 can be assisted by utilization of external sensing devices 202, for example, devices providing echocardiographic capabilities and/or extrathoracic impedance measurements. These embodiments can thus correlate or compare impedance data as sensed by the device 10 with independent external measurements 202 as additional confirmation of the quality of the impedance signals obtained by the device 10. Additional details of various systems and methods of providing connectivity between an implanted device 10 and one or more external sensing devices, such as echocardiographic devices, can be found in the co-owned application A05E4022 that is incorporated herein by reference in its entirety.

If the determination of block 312 is affirmative, a block 314 follows wherein the system and method confirms the ability of the device 10 to utilize impedance signals to at least partially identify valvular events with the impedance signals as previously described. If, however, the determination of block 314 is negative, e.g., that the impedance signals obtained by the device 10 are not of sufficient quality to reliably identify valvular events, a block 313 follows where a decision is made whether an alternative impedance vector or a different combination of impedance vectors should be evaluated for possible better signal quality.

If the decision of block 313 is affirmative, a block 315 follows where an alternative arrangement of impedance sensing vector(s) is selected and reevaluated in block 312. If the result of block 313 is negative, a block 316 follows wherein impedance peaks, such as the peaks 226 are designated for identification of contractile activity of the patient's heart.

Following from block 316 is a confirmation block 318. The confirmation block 318 generally verifies that the device 10 is able to reliably identify cyclical contraction/relaxation via observation of one or more impedance vectors. In one implementation, block 318 can simply compare a count/rate of the cardiac contractions/relaxations obtained from impedance measurements to a count/rate of cardiac depolarizations/repolarizations from IEGM sensing.

If the device 10 is not able to reliably track cardiac activity via impedance measurements, a block 319 follows from a negative decision of block 318. In block 319, the device 10 operates as described above to perform ongoing monitoring of the patient's activity and to generate and deliver therapeutic stimulation as indicated. Block 319 also implements a closed-loop or self-programming algorithm to induce the patient's physiologic performance towards a predefined template of that activity. Such a template can be based at least partially on clinical observations of healthy persons and/or patients exhibiting reversible cardiomyopathy. Such third parties can be referred to as exhibiting eucontractile activity.

Such third parties can also be matched with the patient to have similar physiologic geometries, mass, etc. as the treated patient. Additional details of generating and employing such template data can be found in the co-owned application Ser. No. 11/539,837, filed Oct. 9, 2006, entitled "INDIVIDU-ALLY ADAPTED CARDIAC ELECTRO-MECHANICAL SYNCHRONIZATION THERAPY" which in incorporated herein in its entirety by reference.

However, following from either block 314 or an affirmative result of decision block 318, the system and method 300 includes a block 320 wherein the device 10 proceeds with monitoring of the patient's condition and generation and delivery of indicated therapy as previously described. As also previously noted, at least certain embodiments are directed to more accurately refining or optimizing the programming of a set of variable operational parameters to improve the efficacy of therapy delivery for the patient. At least certain embodiments are also directed to performing such optimization in a more timely manner and in a manner reducing time burdens and inconvenience to attending clinical personnel and to the patient.

Accordingly, in certain embodiments the ongoing monitoring and delivery of therapy to the patient of block 320 includes aspects of closed loop or self-programming of the device 10 as a stochastic system. A stochastic system is a non-deterministic system or a system in which outputs are not fully predictable by known controllable inputs. Thus, in block 320, the device 10 operates autonomously to improve the patient's variable and partially unpredictable cardiac performance by at least periodically self-evaluating that performance and making any indicated changes in a set of a plurality of adjustable operating parameters. Block 320 provides dynamic closed-loop programming in that the device 10 can self-adjust its operation towards a dynamically variable improved level of performance. Additional details and embodiments of systems and methods for providing closed loop or self-programming of an implantable therapy device, such as the device 10, that can be advantageously employed with the embodiments described herein can be found in the co-owned application Ser. No. 11/734,117, filed Apr. 11, 2007, entitled "CLOSED LOOP PROGRAMMING FOR INDIVIDUAL ADJUSTMENT OF ELECTRO-MECHANICAL SYNCHRONY" and co-owned application Ser. No. 11/478,905, filed May 15, 2007, entitled "ASSESSMENT OF IMPEDANCE PARAMETERS AND CLOSED LOOP PROGRAMMING OF AN IMPLANTABLE THERAPY DEVICE," which are both incorporated herein by reference in their entirety.

As previously noted, in certain embodiments, the device 10 and system 300 include rate responsive aspects. In one embodiment, the method further includes a block 322 wherein a determination is made whether or not the patient has an elevated metabolic rate. An elevated metabolic rate can be due to an increased level of physical activity, but can also be due to stress and/or medications such as Dobutamine. If the determination of block 322 is negative or in embodiments lacking the block 322, the method 300 proceeds as previously described.

If the evaluation of block 322 is affirmative, the method 300 proceeds to block 306 and otherwise proceeds substantially as previously described. For example, the method 300 will select block 319 or block 320 following from block 314 or 318 depending on the degree of resolution/reliability with which the device 10 is able to discern cardiac activity via impedance measurements. It will be understood that in certain embodiments the method 300 may operate under different conditions when the patient is at rest as opposed to at an elevated metabolic rate. For example, in one embodiment the method may proceed to block 320 via block 314 when the patient is at rest and be limited to operation under block 319 when the patient has elevated metabolic needs.

Figure 8:
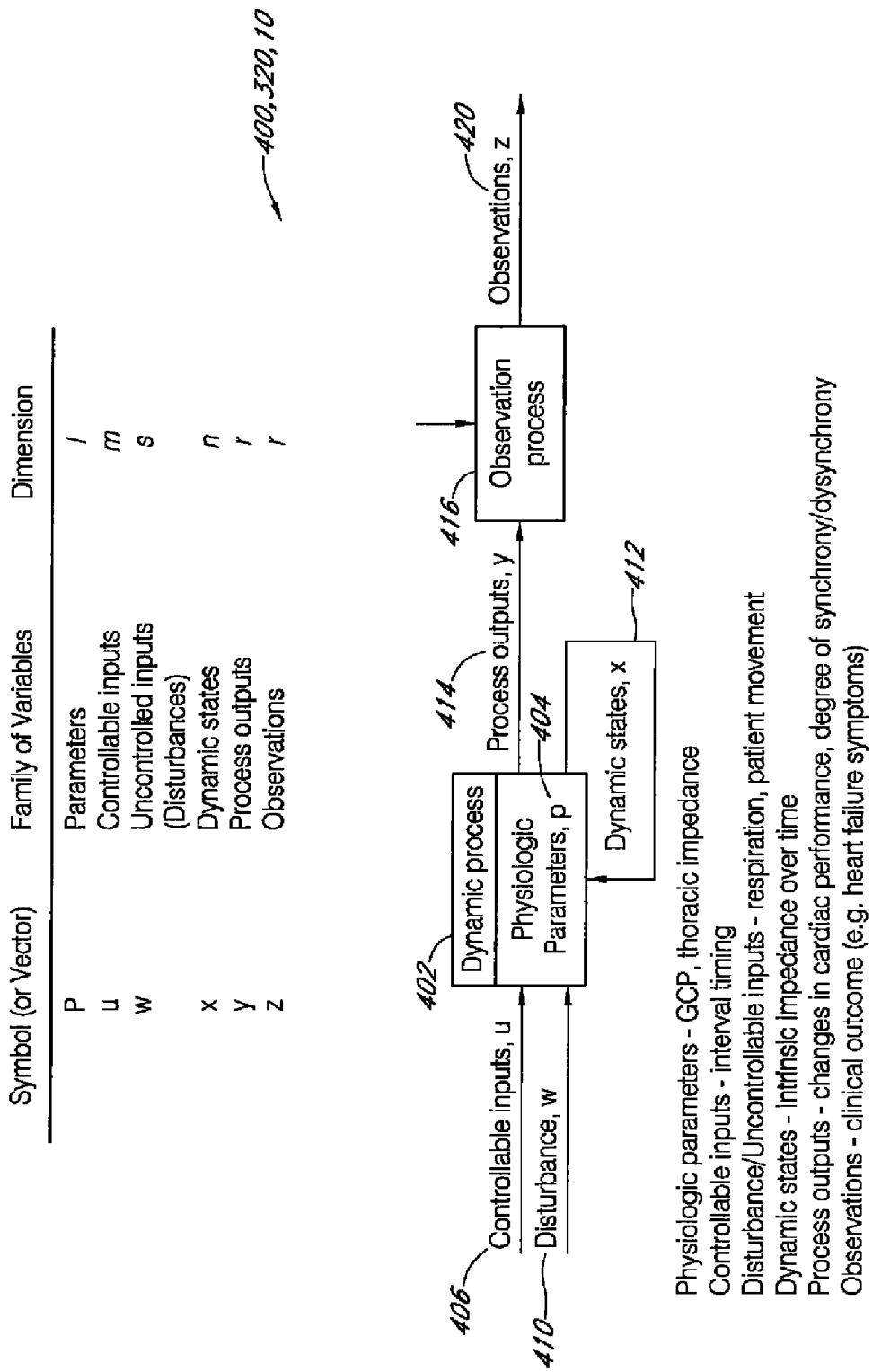
FIG. 8 illustrates one embodiment of a dynamic control system adapted to adjust the operation of an implantable therapy device for an individual patient.

FIG. 8 illustrates that in one embodiment, the implantable device 10 can be considered to comprise a portion of a dynamic control system 400. In this embodiment, the dynamic control system 400 comprises the combination of the intrinsic activity of the patient's heart 12 and the activity of the heart 12 under influence of the therapeutic stimulation provided by the device 10, for example, during block 320. The heart 12 intrinsically functions under a number of control and feedback mechanisms that in a healthy patient provide intrinsic control and feedback mechanisms to automatically regulate the output of the heart 12 to satisfy the person's metabolic needs. In patients with impaired cardiac activity who are provided with embodiments of the implantable therapy device 10, the intrinsic feedback and control mechanisms of the heart 12 operate in conjunction with therapeutic stimulation provided by the device 10 to address deficiencies in the patient's intrinsic self-regulation capabilities. Thus, the intrinsic activity of the patient's heart 12 and the monitoring and therapeutic intervention provided by the device 10, in combination, comprise the dynamic control system 400.

In this embodiment, the dynamic control system 400 defines a stochastic dynamic process 402 corresponding to the patient's cardiac activity. The dynamic process 402 can be characterized by a plurality of physiologic parameters 404, such as global cardiac performance, thoracic impedance, chamber-to-chamber synchrony, ejection fraction, stroke volume, etc. The dynamic process 402 operates under influence of controllable inputs 406 such as interval timing programmed in the device 10. Other controllable inputs 406 can comprise the parameters of therapeutic stimulation such as pulse width and amplitude as well as rate response parameters.

The dynamic process 402 also operates under influence of what can be considered disturbance or uncontrollable inputs in the sense that such inputs are not under the control of the implantable therapy device 10 and are not fully predictable. Such disturbance or uncontrollable inputs 410 can comprise patient respiration, patient movement, influence of medications, stress, etc. The dynamic process 402 also operates under influence of dynamic states 412 following at least partially from one or more of the physiologic parameters 404. For example, one embodiment of dynamic state 412 would comprise the time varying transcardiac impedance over time.

In this embodiment, the dynamic control system 400 and the dynamic process 402 define a plurality of process outputs 414, such as changes in the patient's cardiac performance and relative degree of synchrony/dysynchrony. As previously noted, embodiments are directed to improving the process outputs 414 to result in improved cardiac performance and higher degrees of synchrony/reduction in dysynchrony. The process outputs 414 are themselves dynamic in certain embodiments in that the system 400 can be adapted to constantly attempt to improve or "optimize" the process outputs 414. In these embodiments, the system 400 strives for improvement of the process outputs 414 towards a changing goal rather than a static or predetermined performance goal.

The process outputs 414 can be evaluated as a function of an observation process 416 returning one or more observations 420. The observations 420 can be considered as the clinical outcome of the dynamic control system 400 and in certain embodiments can correspond to heart failure symptoms and/or indications for a revision in the patient's therapy. The observations 420 can of course comprise positive outcomes such as improved remodeling of a previously more dysynchronous heart 12 and/or a reduction in accumulated thoracic fluid, for example as indicated by a change in the offset 221.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A control system for an implantable cardiac therapy device wherein the control system comprises a microcontroller, the implantable therapy device defining a plurality of sensing vectors including at least one impedance sensing vector and the therapy device operating under a set of a plurality of variable operating parameters that define conditions for delivery of therapy by the device and wherein the microcontroller evaluates a signal quality from the at least one impedance sensing vector and, if the quality of the signals is sufficient to discern valvular events, the microcontroller adjusts the set of operating parameters to dynamically improve cardiac performance, including synchrony with valvular events, and if the quality is insufficient to discern valvular events, but sufficient to discern peaks, the microcontroller adjusts the set of operating parameters to dynamically improve cardiac performance independent of valvular events, and if the quality is insufficient to discern peaks, the microcontroller adjusts the set of operating parameters to induce cardiac performance towards a defined performance goal.

2. The control system of claim 1, wherein the microcontroller discriminates the quality of the impedance signals with respect to identification of valvular events via comparison with external measurements.

3. The control system of claim 2, wherein the microcontroller discriminates the quality of the impedance signals with respect to identification of valvular events via comparison with one or more of echocardiographic measurements and extrathoracic impedance measurements.

4. The control system of claim 1, wherein the microcontroller discriminates the quality of the impedance signals with respect to identification of peaks by comparing an impedance peak count with an intracardiac electrogram count.

5. The control system of claim 1, wherein the microcontroller adjusts the set of operating parameters to induce at least one of an increase in an integral of the impedance during contraction and a decrease in an integral of the impedance during relaxation.

6. The control system of claim 1, wherein the microcontroller monitors the patient's activity and evaluates the impedance signals when obtained with the patient at rest.

7. The control system of claim 6, wherein the microcontroller further monitors the patient's respiration and evaluates the impedance signals when obtained with the patient exhibiting one or more of apnea, hypopnea, and end of expiration.

8. The control system of claim 1, wherein the implantable therapy device defines a plurality of impedance vectors.

9. The control system of claim 1, wherein the microcontroller adjusts the set of operating parameters to reduce a post systolic positive impedance.

\* \* \* \* \*